United States Patent [19]

Barnes et al.

[11] Patent Number: 4,674,517
[45] Date of Patent: Jun. 23, 1987

[54] NONINVASIVE ULTRASONIC PROBES

[75] Inventors: Stephen R. Barnes, Seattle; Donald R. Galer, Redmond; Richard S. Leard, Issaquah Island, all of Wash.

[73] Assignee: Lawrence Medical Systems, Inc., Redmond, Wash.

[21] Appl. No.: 764,055

[22] Filed: Aug. 9, 1985

[51] Int. Cl.⁴ .............................................. A61B 10/00
[52] U.S. Cl. .............................................. 128/663
[58] Field of Search .............................. 128/663, 661; 73/861.25

[56] References Cited

U.S. PATENT DOCUMENTS

| | | | |
|---|---|---|---|
| 3,631,849 | 1/1972 | Norris | 128/663 |
| 3,732,532 | 5/1973 | Flaherty | 128/663 |
| 3,777,740 | 12/1973 | Hokanson | 128/663 |
| 3,780,725 | 12/1973 | Goldberg | 128/661 |
| 3,859,984 | 1/1975 | Langley | 128/661 |
| 3,974,692 | 8/1976 | Hassler | 128/663 |
| 4,062,237 | 12/1977 | Fox | 128/663 |
| 4,097,835 | 6/1978 | Green | 128/663 |
| 4,122,713 | 10/1978 | Stasz et al. | 128/663 |
| 4,183,353 | 1/1980 | Gallub | 128/663 |
| 4,217,909 | 8/1980 | Papadofrangakis et al. | 128/663 |
| 4,413,629 | 11/1983 | Durley, III | 128/663 |
| 4,433,691 | 2/1984 | Bickman | 128/663 |
| 4,509,526 | 4/1985 | Barnes et al. | 128/663 |

Primary Examiner—Kyle L. Howell
Assistant Examiner—Francis J. Jaworski
Attorney, Agent, or Firm—Hughes & Cassidy

[57] ABSTRACT

An ultrasonic probe for insonifying the ascending aorta of a supine or reclining human patient. The probe has a head housing transducers for insonifying the patient's ascending aorta and for intercepting doppler-shifted energy reflected from the proximate and distal walls of the ascending aorta and from blood flowing through the aorta. The transducer head is integral with and extends below the handle of the probe, facilitating the manipulation of the probe and alignment of the beam of ultrasonic energy propagated by the probe relative to the ascending aorta of the patient. An oval cross-section and trapezoidal profile allow this to be done with a minimum of discomfort to either the patient or the user of the probe, and an L- or T-shaped handle allows the probe to be positioned and manipulated from a position behind the patient's head and with little or no sight of the patient's suprasternal notch.

4 Claims, 7 Drawing Figures

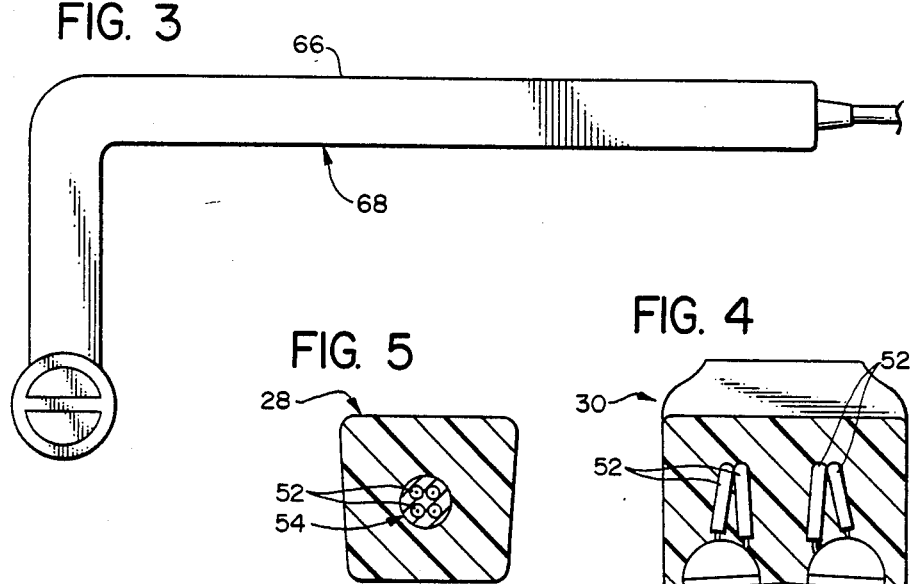
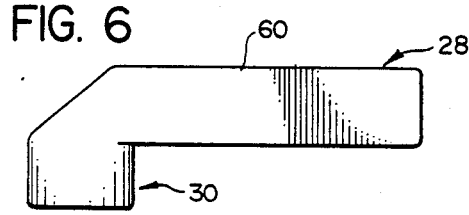
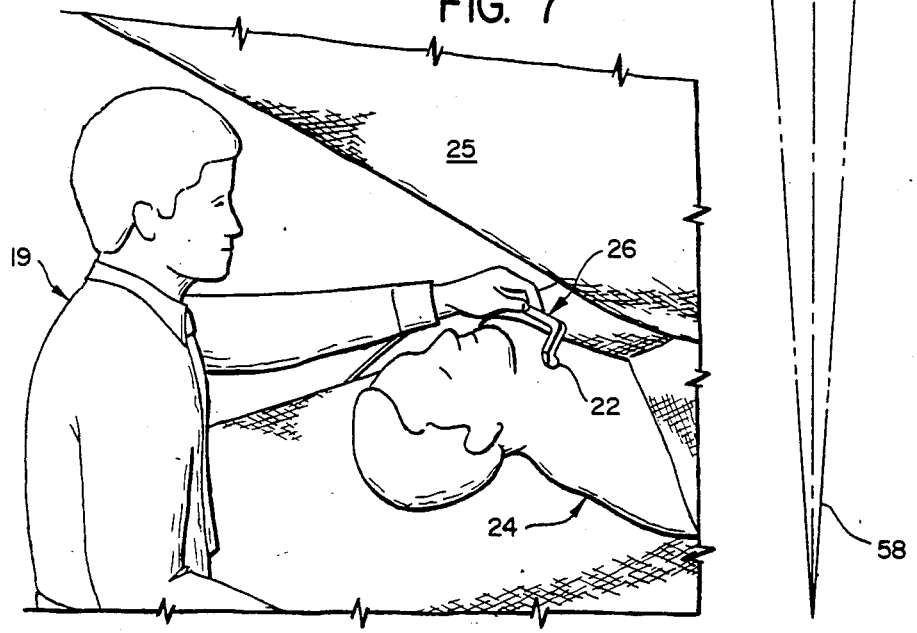

NONINVASIVE ULTRASONIC PROBES

FIELD OF THE INVENTION

The present invention relates to noninvasive ultrasonic probes and, more particularly, to novel, improved probes for insonifying the ascending aorta of a human patient.

BACKGROUND OF THE INVENTIONS

Ultrasonic imaging (or insonification of anatomical structures has come to the fore as a diagnostic technique within the last decade and is also now beginning to be used in monitoring a patient's condition during surgical and other procedures. In the insonification technique, ultrasonic energy is transmitted into a body; and this energy, as reflected from body fluids, organs, tissues, and other anatomical structures on which it impinges, is intercepted. The information contained in the intercepted energy is extracted and processed, providing an indication of the patient's condition. Insonification is commonly used to identify a wide range of physical conditions and/or disorders. For example, it is employed in prenatal examinations of a fetus, diagnosis of abnormalities of cardiac structures, and in the measurement of cardiac output.

It is to the latter application of ultrasonic instrumentation that the present invention is specifically directed. In that application, as envisaged by us, the ascending aorta of the patient is insonified with ultrasonic energy propagated from an ultrasonic energy transmitting transducer probe positioned in his suprasternal notch, and the reflected energy is intercepted by a receiving transducer housed in the head of that probe.

The reflected energy contains information from which the systolic velocity of the blood flowing in the patient's ascending aorta can be calculated. From this parameter and the patient's aortic diameter the patient's cardiac output can be calculated as is explained in U.S. Pat. No. 4,509,526 which issued to Barnes et al on Apr. 9, 1985. U.S. Pat. No. 4,509,526 is assigned to the assignee of this application and is incorporated herein by reference.

Not easily met requirements are imposed on ultrasonic probes employed in the just-described technique for measuring cardiac output.

Ultrasonic probes as disclosed herein will typically be incorporated in equipment which is designed to monitor the cardiac output of a patient during a surgical procedure. The patient is commonly placed in a supine or reclining position during surgery and draped to expose the operating field to guard against infection. The operator of the cardiac output monitoring equipment, normally the anesthesiologist attending the operation, must be able to position and manipulate the ultrasonic probe from his position behind the head of the surgical patient.

During surgical procedures as described above, the head of the ultrasonic probe is visually obscured within the suprasternal notch of the patient and by the surgical drapes. The anesthesiologist or other operator of the cardiac output monitoring equipment will customarily also be monitoring a visual display as he manipulates the probe in order to achieve that orientation of the probe which will result in the ultrasonic beam being propagated in an optimum direction with respect to the patient's ascending aorta. Because of the visual obscuration, and the requirement that the operator be free to monitor a visual display, ultrasonic probes with which we are concerned must also be so designed that they can be positioned and manipulated primarily be feel.

It is furthermore required that the operator be comfortable while the ultrasonic probe is in use because surgical procedures can take several hours or more if the surgery is extensive.

Patient comfort is a requirement which should not be underestimated. If the patient moves while his cardiac output is being monitored, the transducer head of the ultrasonic probe may shift, causing erroneous data to be generated. Consequently, it is necessary that the patient remain reasonably still during the monitoring procedure; and this requires that the patient not be made uncomfortable by the probe, especially if he is conscious while it is being used.

The just-discussed combination of requirements are not met by the ultrasonic probes described in U.S. Pat. No. 4,582,066 issued Apr. 15, 1986, to Barnes et al. for ULTRASONIC TRANSDUCER PROBE because of the difficulty experienced in manipulating a probe with a straight handle from behind the patient's head. This makes it at least extremely hard to position and manipulate the probe with any degree of accuracy and can lead to both patient and operator discomfort.

SUMMARY OF THE INVENTION

All of the foregoing requirements and desiderata of a noninvasive ultrasonic probe are abundantly met by the novel probes disclosed herein. In general, those probes have a transducer head which can be positioned and manipulated within the suprasternal notch of the patient being monitored and a handle by which the probe can be so positioned and manipulated.

The operator-engageable handles of our novel probes have integral proximate and distal portions which meet at a severe, typically right, angle, giving the handle an L-shaped configuration when viewed from above or below (all orientations specified herein are those assumed when the probe is in use). This configuration makes it possible for the anesthesiologist or other operator of the cardiac output monitoring equipment to position and manipulate the probe from his position behind the reclining or supine patient's head with ease and with little or no reliance on the sense of sight. And, because the probe can be easily positioned and manipulated from this location, the operator can hold the probe in position in the patient's suprasternal notch for a lengthy period of time, if necessary, without his hand or arm becoming unduly fatigued.

The transducer head is an integral part of the probe. It is located at, and extends downwardly and at right angles from, its juncture with the free end of the handle's proximate portion. This depending orientation of the transducer head relative to the handle of the probe is important. It provides sufficient clearance between the patient and the probe handle to accommodate the operator's fingers when the transducer head is positioned in the patient's suprasternal notch. This is important in terms of operator comfort and in properly positioning and manipulating the ultrasonic probe.

It is preferred that both the proximate and distal portions of the probe handle have a generally rectangular cross-sectional configuration or one in which the sides of the handle converge slightly toward its bottom. These configurations provide four flat surfaces for the operator's thumb and fingers, promoting optimal positioning and accurate manipulation of the probe using the sense of feel alone, or feel plus a limited use of the visual sense.

In their preferred forms, the transducer heads of the ultrasonic probes disclosed herein have an oval cross-sectional configuration and a generally trapezoidal profile. This combination of external configurations facilitates rotational and rectilinear manipulation of the transducer head within the patient's suprasternal notch with minimal discomfort to the patient (for the reasons discussed above, minimal interference with patient comfort is an important advantage of a suprasternal notch probe).

To further promote both operator and patient comfort, rounded edges are provided between intersecting surfaces throughout the probe.

Typically, two D-shaped piezoelectric transducers will be mounted in side-by-side relationship at the lower or exposed end of the transducer head. These propagate ultrasonic energy in a path paralleling the patient's ascending aorta and intercept frequency-shifted energy reflected from the aortic structure and blood flowing through that vessel. This arrangement is not essential, however; it can be replaced with a single transducer as is conventional in a pulse echo system, for example.

In the above-described dual transducer arrangement, the transducers are preferably canted toward each other. This guarantees that the bulk of the energy reflected from the insonified anatomical structure of the patient will be intercepted by the transducer employed for that purpose and that the data carried by the intercepted signal will therefore be complete and accurate.

OBJECTS OF THE INVENTION

From the foregoing it will be apparent to the reader that one important, primary object of the invention resides in the provision of novel, improved, noninvasive ultrasonic probes.

A related, important and primary object of the invention resides in the provision of noninvasive ultrasonic probes which can be inserted within a supine or reclining patient's suprasternal notch and then manipulated within that notch with facility by an operator positioned behind the patient's head even though the patient may be draped and otherwise prepared for surgery.

Still another related, also important and primary object of our invention resides in the provision of noninvasive ultrasonic probes as identified in the preceding object which can be accurately positioned and manipulated primarily, or entirely, by the sense of touch and without causing discomfort to either the operator or the patient.

Other important objects and features and additional advantages of the invention will be apparent from the foregoing and the appended claims and as the ensuing detailed description and discussion proceeds in conjunction with the accompanying drawing.

BRIEF DESCRIPTION OF THE DRAWING

In the drawing:

FIG. 3 is a bottom view of the probe;

FIG. 4 is a section through the probe taken substantially along line 4—4 of FIG. 3;

FIG. 5 is a section through the probe taken substantially along line 5—5 of FIG. 3;

FIG. 6 is an end view of the probe; and

FIG. 7 is a view similar to FIG. 1 but showing an ultrasonic probe as illustrated in FIG. 2 positioned within the supine patient's suprasternal notch by an operator standing behind his head.

DETAILED DESCRIPTION OF PRESENTLY PREFERRED EMBODIMENTS

Figure 1:
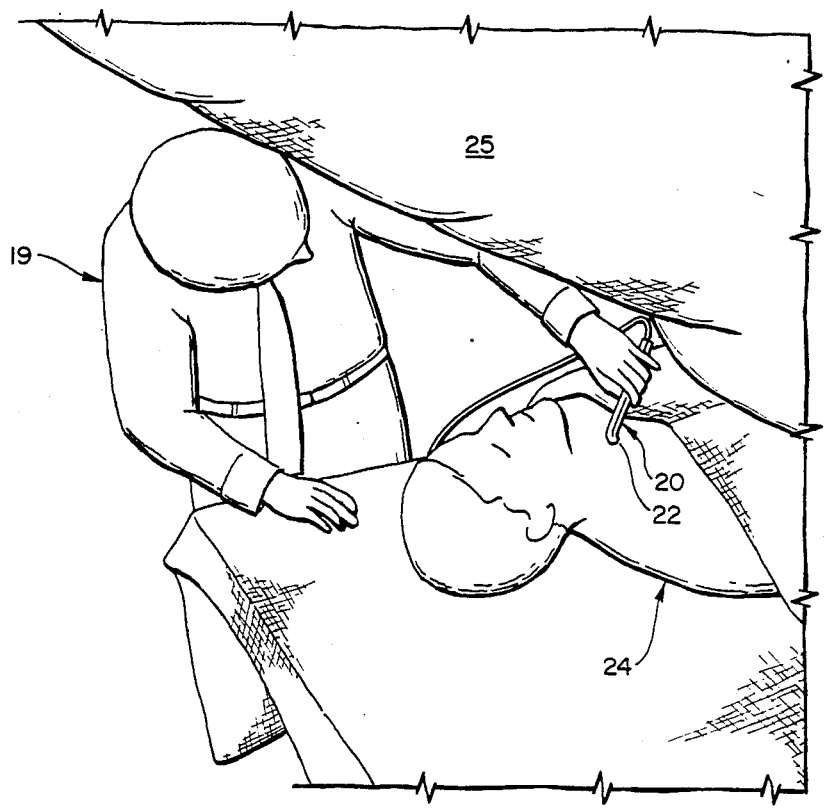
FIG. 1 is a pictorial view illustrating the difficulty experienced in positioning and manipulating an ultrasonic probe as disclosed in U.S. Pat. No. 4,582,066 within the suprasternal notch of a supine patient from a position behind and facing the patient's head.

Referring now to the drawing, FIG. 1 shows, pictorially, an operator 19 attempting to position a straight-handled ultrasonic probe 20 as disclosed in U.S. Pat. No. 4,582,066 within the suprasternal notch 22 of a supine patient 24. It will be appreciated from FIG. 1 that this is an extremely awkward procedure which is compounded by surgical drapes 25. Furthermore, this awkwardness readily leads to undue pressure being exerted on the patient's throat and the patient consequently may experience discomfort and move in an effort to alleviate the pain. This is undesirable because, as discussed above, movement of the patient can result in erroneous data being transmitted from probe 20 to the cardiac output monitoring apparatus in which the probe is incorporated (not shown).

It will further be appreciated that the akwardness of positioning and manipulating ultrasonic probe 20 can cause the operator's hand and/or arm to cramp or otherwise cause operator discomfort. This, too, is disadvantageous, particularly when a measurement procedure of extended duration is involved.

In FIG. 1, the operator is attempting to manipulate prior art probe 20 from a position beside, and near the head of, the patient. The above-discussed complications this introduces are compounded when the operator moves to that station behind the patient's head at which he must be during an actual surgical procedure so that he can carry out his functions and so that he will not interfere with the surgical team.

And, it will be appreciated from FIG. 1 that the operator's vision of the patient's suprasternal notch is almost totally obscured from this position that he normally takes, and that he must consequently position and manipulate probe 20 primarily by the sense of feel, especially as he will be visually monitoring the cardiac output measuring apparatus and/or other equipment while he is doing so. Because of the awkwardness experienced in manipulating probe 20 from the position in question, it is at best extremely difficult to position and manipulate the probe with any degree of accuracy at all.

Figure 2:
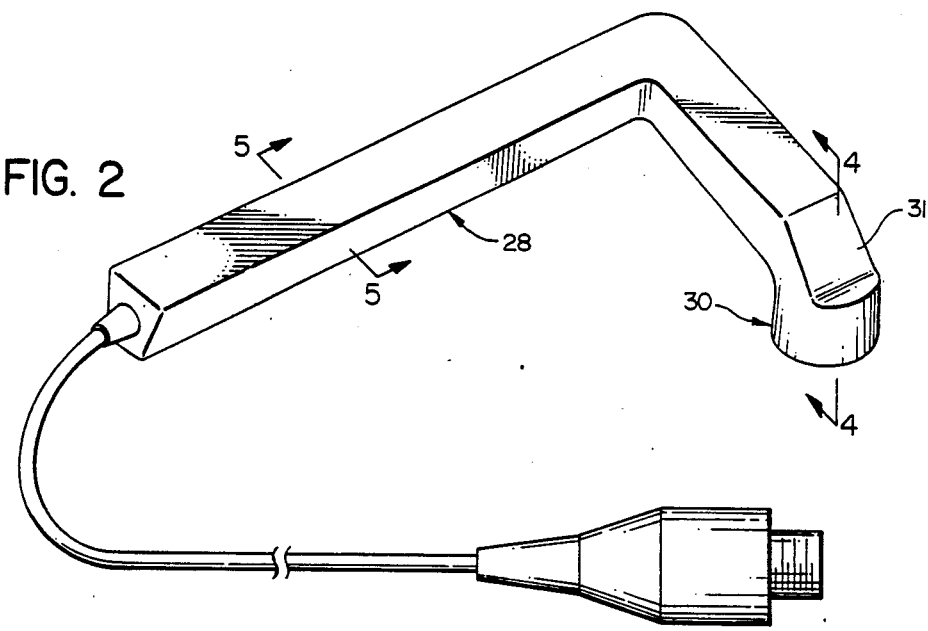
FIG. 2 is a perspective view of an ultrasonic probe embodying the principles of the present invention.

The foregoing drawbacks of probe 20 are completely alleviated by the novel ultrasonic probe embodying the principles of the present invention which is illustrated in FIGS. 2 and 3 and identified by reference character 26. Turning now to those figures, probe 26 includes a handle 28 and a transducer head 30 integral therewith. Transducer head 30 has a sloping top wall 31 and curved side walls 32 giving the transducer head a generally oval cross-sectional configuration as shown in FIG. 3 and a trapezoidal profile as shown in FIG. 6. The bottom or lower end of the transducer head is essentially flat when viewed from the side; it has a shallow V-configuration when seen from the front (FIG. 6).

In the embodiment of the invention shown in the drawing, the lower end 34 of transducer head 30 extends approximately 0.44" below the bottom side or surface 36 of probe handle 28. This is an important feature of probe 26 as it furnishes sufficient clearance for the operator to wrap his fingers around the handle 28 of probe 26 when the head of the probe is positioned in the patient's suprasternal notch. This facilitates the tactile positioning and manipulation of the probe within the patient's suprasternal notch.

Flat, D-shaped transducers 38 and 40 are flush-mounted in cavities 42 and 44 in the lower end 34 of transducer head 30 with the transducers canted toward a longitudinal plane 46 extending vertically through the transducer head as is shown in FIG. 4. The included angle "A" between the transducers 38 and 40 will typically be approximately 174°.

The illustrated transducers 38 and 40 are of the conventional piezoelectric crystal type; and these will, accordingly, not be described further herein. They can be cemented in place by an appropriate adhesive, for example.

Referring now specifically to FIG. 4, ultrasonic energy is propagated from transducer 38 along path 48. This energy, doppler-shifted in frequency, is reflected from the patient's aortic structure and the blood flowing through that vessel back to receptor transducer 40 along path 50.

Transducers 38 and 40 are connected to an external energy source (not shown) through leads 52 incorporated in a conventional insulated cable 54. This cable passes through the head 30 and handle 28 of probe 26 (see FIGS. 4 and 5) and, externally of the probe, terminates in a conventional six-prong connector 56.

As shown in FIG. 4, the path 48 of the propagated ultrasonic energy and the path 50 of the reflected, frequency-shifted energy converge in a focal zone 58 which embraces the patient's ascending aorta. U.S. Pat. No. 4,582,066 points out that, in a probe of the character under discussion, this zone has a focal point which is preferably approximately seven centimeters from the lower end 34 of transducer head 30. This goal can be realized by configuring the lower end of probe 20 so that the above-discussed angle A between the two transducers 38 and 40 will be the preferred 174°.

Referring now primarily to FIGS. 2 and 3, the handle 28 has a proximate, horizontal portion 60 and, extending at a severe, preferably 90°, angle therefrom, a second, also horizontal, distal portion 62.

As is readily apparent from the drawings, the preferred cross-sectional configuration of handle 28 is one which is essentially approximately rectangular but with the side walls 66 and 68 of the handle's distal portion 28 tapering slightly toward each other from the top toward the bottom of the handle to provide the most secure grasp and optimal operator comfort.

This is not essential, however; and strictly rectangular and other polygonal configurations can be employed, if desired. Also, configurations such as circular may be employed with one or more protruding grips being provided in such cases to furnish a secure operator grip.

These novel ultrasonic probe handle configurations just discussed are an important feature of our invention because, as shown in FIG. 7, they allow the operator to position the transducer head 30 of the probe 26 in the patient's suprasternal notch and to rotate, move rectilinearly, and otherwise manipulate its transducer head 30 with facility and without the strain or other discomfort he would experience in attempting to make the same manipulations with a straight-handled probe as disclosed in U.S. Pat. No. 4,582,066 from his position behind a patient's head. These advantages and the minimization of patient discomfort are also promoted by the combined effects of this L-shaped probe handle configuration, the orthagonal relationship among the two sections of the handle and the transducer head, and the curvilinear cross-sectional configuration and trapezoidal profile of the latter.

It will be manifest from the foregoing that accurate positioning of ultrasonic probe 26 is paramount in obtaining data which accurately indicates the diameter of the patient's ascending aorta. In the operating arena this requires manipulation of transducer head 30 with little or no visual assistance and without discomfort to the patient, goals which are met by probe 26 because of the shape of the transducer head, the multiple graspable surfaces and L-shaped configuration of the probe handle, and the use of rounded edges to avoid discomfort to both the patient and the person manipulating the probe.

In positioning and aligning the transducer head 30 or ultrasonic probe 26 in a patient's suprasternal notch, the anesthesiologist or other person employing the probe reaches past the head of the patient and introduces the transducer head 30 of the probe within the patient's suprasternal notch (see FIG. 7). This maneuver is typically effected while the operator's attention is directed to a visual display of the cardiac output equipment and other monitors (the former assists him in properly positioning the probe). Thereafter, the transducer head may be rotated, shifted rectilinearly, and tilted, again with attention focused on the visual display, until display shows that the position of the probe has been optimized.

With the operator's fingers and thumb pressed against the distal handle portion 62 of probe 20, a secure grip which optimizes control over these manipulations of the probe with minimal, or even no, view of the patient's suprasternal notch or transducer head 30 is conveniently available.

The ultrasonic probe 26 illustrated in FIGS. 2–7 and discussed above is configured for use by a right-handed operator positioned behind the head of a supine or reclining patient. An L-shaped, mirror image configuration is provided for left-handed operators. Alternatively, a handle with a T-shaped configuration may be employed so that the probe can be used by either a left-handed or right-handed operator.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description; and all changes which come within the meaning and range of equivalency of the claims are therefore intended to be embraced therein.

What is claimed and desired to be secured by Letters Patent of the United States is:

1. An ultrasonic probe for insonifying the ascending aorta of a supine or reclining human patient from a location within the suprasternal notch of the patient, said probe comprising a transducer head and an elongated handle; said transducer head housing transducer means for propagating ultrasonic energy and for intercepting frequency-shifted, reflected radiant energy; said handle having a proximate portion and a distal portion and a non-circular cross-sectional configuration with at least one longitudinal edge which furnishes a gripping surface and thereby facilitates tactile positioning of said probe; said transducer head being integral with the handle of said probe at the exposed end of the said proximate portion thereof; said transducer head having a generally arcuate cross-sectional configuration and a generally trapezoidal profile; said transducer head being oriented at right angles to said proximate portion of said handle and having an exposed, patient contacting end in which said transducer means are located, thereby facilitating the orientation of the transducer means housed in said head relative to the ascending aorta of the patient; and said distal end portion of the elongated probe handle being integral with and immovably oriented at a severe angle relative to the proximate end of that handle, and lying in the same plane as the proximate end of the handle, whereby the transducer head of said probe can be placed with facility within the suprasternal notch of the patient by an operator positioned behind the head of said patient.

2. An ultrasonic probe as defined in claim 1 wherein said handle has a generally rectangular cross-sectional configuration providing four flat grippable surfaces for facilitating the positioning and manipulation of the probe and rounded corners at the intersections of said surfaces for making said handle comfortable to grip.

3. An ultrasonic probe as defined in claim 1 wherein said transducer head has a generally oval cross-section configuration with the major axis thereof oriented substantially normal to the longitudinal axis of the proximate handle portion, said transducer means comprising first and second transducers and said probe further comprising means mounting said transducers in side-by-side relationship in said head.

4. An ultrasonic probe as defined in claim 3 wherein each of said transducers is a piezoelectric crystal that has a D-shaped cross-sectional configuration.

* * * * *